(12) United States Patent
Huffer et al.

(10) Patent No.: US 11,911,144 B2
(45) Date of Patent: Feb. 27, 2024

(54) ULTRASOUND IMAGING SYSTEM AND INTERVENTIONAL MEDICAL DEVICE FOR USE THEREWITH

(71) Applicant: C. R. Bard, Inc., Franklin Lakes, NJ (US)

(72) Inventors: Katherine A. Huffer, Chandler, AZ (US); Bryon E. Pelzek, Gold Canyon, AZ (US); Ranjani Sampath Kumaran, Tempe, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 53 days.

(21) Appl. No.: 16/801,835

(22) Filed: Feb. 26, 2020

(65) Prior Publication Data

US 2020/0187826 A1 Jun. 18, 2020

Related U.S. Application Data

(63) Continuation-in-part of application No. 16/638,326, filed as application No. PCT/US2017/047898 on Aug. 22, 2017, now abandoned.

(51) Int. Cl.
*A61B 5/06* (2006.01)
*A61B 5/00* (2006.01)
*A61B 34/20* (2016.01)

(52) U.S. Cl.
CPC ............ *A61B 5/066* (2013.01); *A61B 5/0013* (2013.01); *A61B 5/0022* (2013.01); *A61B 5/062* (2013.01);
(Continued)

(58) Field of Classification Search
CPC ..... A61B 5/066; A61B 5/0013; A61B 5/0022; A61B 5/062; A61B 34/20;
(Continued)

(56) References Cited

U.S. PATENT DOCUMENTS 5,769,843 A 6/1998 Abela et al.
5,982,297 A * 11/1999 Welle ..................... G08C 23/02
367/134
(Continued)

FOREIGN PATENT DOCUMENTS

EP 2647344 A1 10/2013
JP 2000023979 A 1/2000
(Continued)

OTHER PUBLICATIONS

März, K., Franz, A.M., Seitel, A. et al. Interventional real-time ultrasound imaging with an integrated electromagnetic field generator. Int J CARS 9, 759-768 (2014). https://doi.org/10.1007/s11548-014-0990-3 (Year: 2014) (Year: 2014).*
(Continued)

*Primary Examiner* — Yi-Shan Yang
*Assistant Examiner* — Nicholas A Robinson
(74) *Attorney, Agent, or Firm* — Dinsmore & Shohl LLP

(57) ABSTRACT

An imaging system includes an ultrasound probe, and an interventional medical device having a tracking device. The ultrasound probe includes an ultrasound transducer to generate an ultrasound field-of-view, a tracking field generator to generate an electromagnetic locator field, and a wireless receiver. The interventional medical device has a distal end portion to which the tracking device is mechanically coupled. The tracking device includes a plurality of tracking coils, a wireless transmitter, and a power supply circuit. The plurality of tracking coils interact with the electromagnetic locator field to determine a location within the electromagnetic locator field and to generate tracking data. The wireless transmitter is configured to transmit the tracking data from the tracking device of the interventional medical device to the wireless receiver of the ultrasound probe. The power
(Continued)

supply circuit is configured to supply electrical power to the wireless transmitter of the tracking device.

18 Claims, 11 Drawing Sheets

(52) U.S. Cl.
CPC ...... *A61B 34/20* (2016.02); *A61B 2034/2063* (2016.02)

(58) Field of Classification Search
CPC .......... A61B 2034/2063; A61B 8/0841; A61B 8/4245; A61B 8/467; A61B 5/061; A61B 34/25; A61B 2017/00221; A61B 2017/3413; A61B 2034/2051; A61B 2034/2072; A61B 2090/378; A61B 34/22
See application file for complete search history.

(56) References Cited

U.S. PATENT DOCUMENTS

| | | | |
|---|---|---|---|
| 6,248,074 B1 | 6/2001 | Ohno et al. | |
| 6,522,907 B1 | 2/2003 | Bladen et al. | |
| 6,684,094 B1 | 1/2004 | Lehr et al. | |
| 6,716,166 B2 | 4/2004 | Govari | |
| 6,773,402 B2 | 8/2004 | Govari et al. | |
| 7,713,210 B2 | 5/2010 | Byrd et al. | |
| 7,806,829 B2 | 10/2010 | Hauck | |
| 7,848,789 B2 | 12/2010 | Govari et al. | |
| 7,969,142 B2 | 6/2011 | Krueger et al. | |
| 8,041,413 B2 | 10/2011 | Barbagli et al. | |
| 8,086,298 B2 | 12/2011 | Whitmore, III et al. | |
| 8,428,691 B2 | 4/2013 | Byrd et al. | |
| 8,461,978 B2 | 6/2013 | Garner et al. | |
| 8,945,147 B2 | 2/2015 | Ritchey et al. | |
| 9,024,624 B2 | 5/2015 | Brunner | |
| 9,055,883 B2 | 6/2015 | Tgavalekos et al. | |
| 9,173,638 B2 | 11/2015 | Govari et al. | |
| 9,289,187 B2 | 3/2016 | Owen et al. | |
| 9,308,041 B2 | 4/2016 | Altmann et al. | |
| 9,375,163 B2 | 6/2016 | Ludwin et al. | |
| 9,474,465 B2 | 10/2016 | Ashe | |
| 9,707,041 B2 | 7/2017 | Iustin et al. | |
| 9,901,324 B2 | 2/2018 | Cho et al. | |
| 2003/0191547 A1* | 10/2003 | Morse ................ | A63B 24/0021 700/91 |
| 2006/0214848 A1* | 9/2006 | Roberts ................... | G01S 11/02 342/458 |
| 2009/0023400 A1* | 1/2009 | Nishio .................... | H03B 5/36 331/155 |
| 2009/0289621 A1* | 11/2009 | Petersen .............. | A61B 5/1079 324/207.16 |
| 2010/0037902 A1* | 2/2010 | Wirtz ................... | G01R 33/287 128/899 |
| 2010/0305429 A1 | 12/2010 | Shachar et al. | |
| 2012/0035468 A1 | 2/2012 | Ritchey et al. | |
| 2012/0143029 A1 | 6/2012 | Silverstein et al. | |
| 2013/0303886 A1 | 11/2013 | Ludwin et al. | |
| 2014/0107487 A1 | 4/2014 | Kim et al. | |
| 2014/0121489 A1 | 5/2014 | Kommu Chs | |
| 2015/0073266 A1 | 3/2015 | Brannan et al. | |
| 2015/0320386 A9 | 11/2015 | Liu | |
| 2016/0000399 A1* | 1/2016 | Halmann ........... | A61B 17/3403 600/461 |
| 2016/0007842 A1 | 1/2016 | Govari et al. | |
| 2016/0029998 A1 | 2/2016 | Brister et al. | |
| 2016/0081584 A1 | 3/2016 | Clark et al. | |
| 2016/0220228 A1 | 8/2016 | Pandey et al. | |
| 2016/0331351 A1 | 11/2016 | Guracar | |
| 2016/0338675 A1 | 11/2016 | Kubota | |
| 2017/0105706 A1 | 4/2017 | Berger et al. | |
| 2017/0281029 A1 | 10/2017 | Messerly et al. | |
| 2020/0008775 A1* | 1/2020 | Erkamp .............. | A61B 8/0841 |
| 2020/0045537 A1* | 2/2020 | Colombo ............. | H04W 12/71 |

FOREIGN PATENT DOCUMENTS

| | | |
|---|---|---|
| WO | 2013006817 A1 | 1/2013 |
| WO | 2016081023 A1 | 5/2016 |

OTHER PUBLICATIONS

Kshirsagar A V, Duttagupta S P and Gangal S A 2008 Design of MEMS cantilever—hand calculation Sensors Transducers J. 91 55-69 (Year: 2008).*

Marz K et al: Interventional real-time ultrasound imaging with an integrated electromagnetic field generator, International Journal of Computer Assisted Radiology and Surgery, Springer, DE, vol. 9, No. 5, Mar. 25, 2014 (Mar. 25, 2014), pp. 759-768, XP035400415, ISSN: 1861-6410' DOI: 10.1007/S11548-014-0990-3 [retrieved on Mar. 25, 2014].

Marz, K., Franz, A. M. ,Seitel ,A. et al. Interventional real-time ultrasound imaging with an integrated electromagnetic field generator. Lnt J CARS 9, 759-768 (2014). https://doi.org/10.1007/s11548-014-0990-3 (Year:2014).

Franz, Alfred Michael. Workflow-integrated Electromagnetic Tracking for Navigated Ultrasound-guided Interventions (2015). https://archiv.ub.uni-heidelberg.de/volltextserver/19996/ (Year: 2015).

* cited by examiner

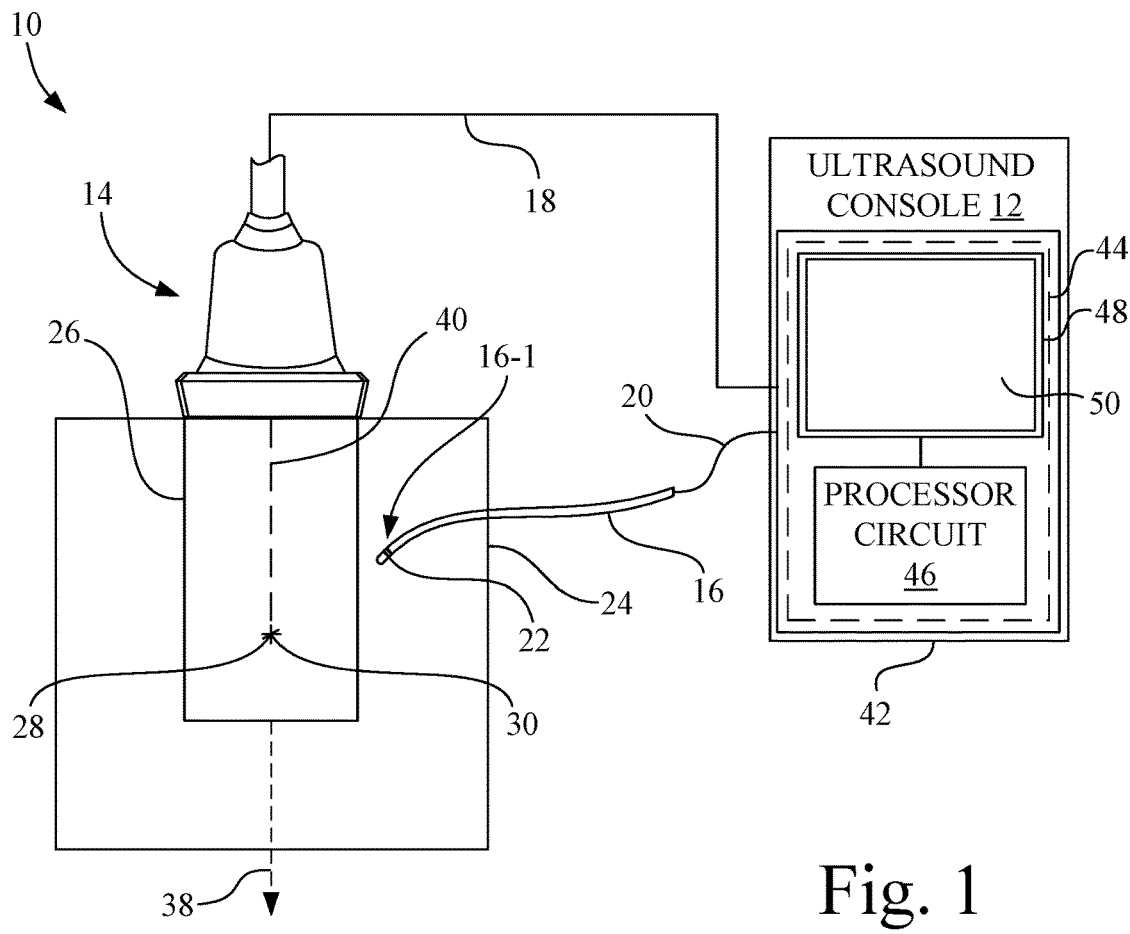
Fig. 1
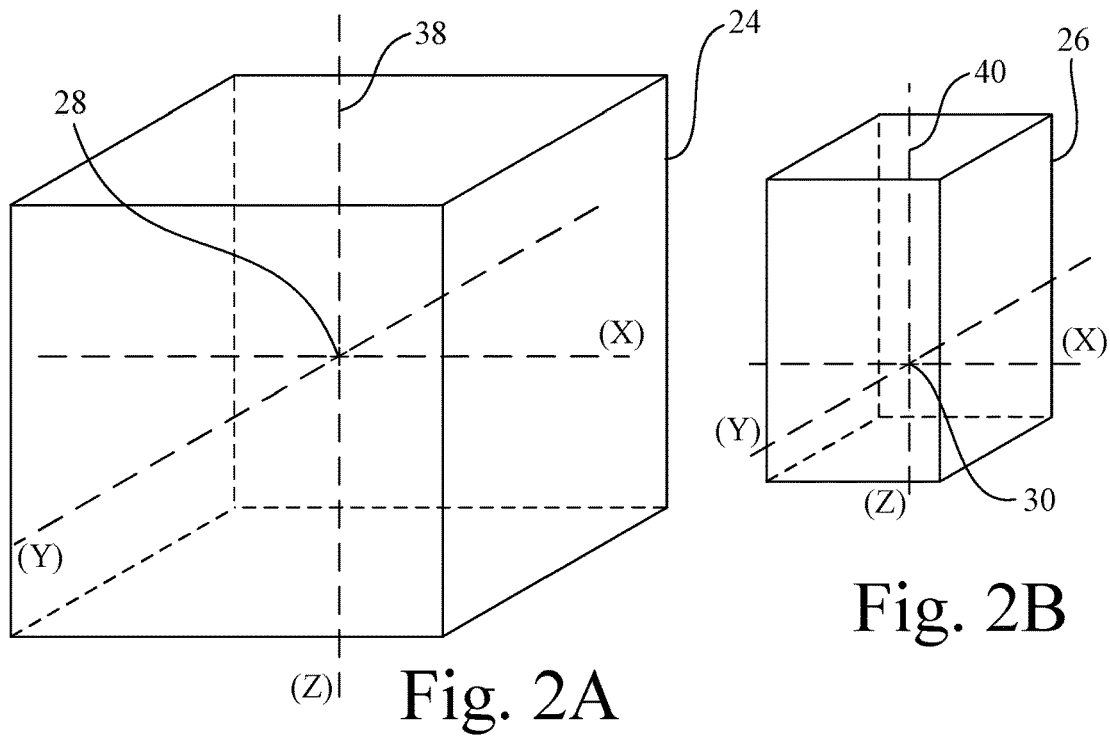
Fig. 2A
Fig. 2B

ULTRASOUND IMAGING SYSTEM AND INTERVENTIONAL MEDICAL DEVICE FOR USE THEREWITH

CROSS-REFERENCE TO RELATED APPLICATIONS

This application is a continuation-in-part of U.S. patent application Ser. No. 16/638,326 filed Feb. 11, 2020, which is a U.S. national phase of International Application No. PCT/US2017/047898, filed Aug. 22, 2017, each of which is incorporated herein by reference.

TECHNICAL FIELD

The present invention relates to an ultrasound imaging system having an ultrasound probe configured to facilitate tracking of an interventional medical device, and which, in some embodiments, may include wireless communication of tracking data from the interventional medical device to the ultrasound probe.

BACKGROUND ART

An electromagnetic location tracking system, such as the Aurora® Electromagnetic Tracking System available from Northern Digital Inc. (NDI) includes a stationary electromagnetic (EM) field generator that is used to track the location of a medical device having a tracking element, which has been inserted into a patient. The EM field generator generates a base electromagnetic field that radiates in a fixed orientation relative to the patient to facilitate electromagnetic spatial measurement.

In particular, the EM field generator is placed near an area of interest (e.g., leg, abdomen, etc.) of the patient, such that a region of interest lies within a detection volume of the generated EM field. Once placed, the EM field generator remains stationary relative to the region of interest, i.e., the patient. The EM locator field is used in determining the location within the patient of a tracked element of the medical device that is inserted into a vessel or cavity of the patient. For example, the medical device may be a catheter or a guide wire, which has an elongate body having a distal tip and a distal end portion, and having a tracking element, such as a magnetic sensor, mounted at the distal end portion. The magnetic sensor is used in generating tip location data based on the EM locator field as the medical device is moved within the patient.

One prior system, described in PCT/US2015/018068 which is assigned to the assignee of the present invention, utilizes the electromagnetic tracking system in conjunction with both an interventional medical device and an ultrasound probe. In particular, the stationary electromagnetic field generator tracks the location of both the interventional medical device and an ultrasound probe using the EM locator field, and the system identifies and displays two-dimensional ultrasound image slices that include an image of the distal tip of the interventional medical device.

What is needed in the art is an ultrasound imaging system having an ultrasound probe configured to facilitate tracking of an interventional medical device, and which, in some embodiments, may include wireless communication of tracking data from the interventional medical device to the ultrasound probe.

SUMMARY OF INVENTION

The present invention provides an ultrasound imaging system having an ultrasound probe configured to facilitate tracking of an interventional medical device, and which, in some embodiments, may include wireless communication of tracking data from the interventional medical device to the ultrasound probe.

The invention in one form is directed to an ultrasound probe for use in an ultrasound imaging system. The ultrasound probe includes a probe housing. An ultrasound transducer array is mounted to the probe housing. The ultrasound transducer array is configured to generate an ultrasound field-of-view volume. An electromagnetic locator field generator also is mounted to the probe housing. The electromagnetic locator field generator is configured to generate an electromagnetic locator field volume.

The invention in another form is directed to an ultrasound probe for use in an ultrasound imaging system. The ultrasound probe includes a probe housing. An ultrasound transducer array is mounted to the probe housing. The ultrasound transducer array is configured to generate an ultrasound field-of-view volume. A plurality of electromagnetic coils also is mounted to the probe housing. The plurality of electromagnetic coils is configured to generate an electromagnetic locator field volume wherein an entirety of the ultrasound field-of-view volume is located within the electromagnetic locator field volume.

The invention in another form is directed to an ultrasound imaging system that includes an ultrasound console having a graphical user interface. An interventional medical device is communicatively coupled to the ultrasound console. The interventional medical device has a tracking element. An ultrasound probe is communicatively coupled to the ultrasound console. The ultrasound probe includes a probe housing. An ultrasound transducer array is mounted to the probe housing. The ultrasound transducer array is configured to generate an ultrasound field-of-view volume. An electromagnetic locator field generator includes a plurality of electromagnetic coils that are mounted to the probe housing. The plurality of electromagnetic coils is configured to generate an electromagnetic locator field volume for identifying a location of the tracking element of the interventional medical device within the electromagnetic locator field volume.

The invention, in still another form, is directed to an imaging system that includes an ultrasound probe and an interventional medical device having a tracking device, wherein tracking data is transferred wirelessly from the interventional medical device to the ultrasound probe. The ultrasound probe includes an ultrasound transducer configured to generate an ultrasound field-of-view, a tracking field generator to generate an electromagnetic locator field, and a wireless receiver. The interventional medical device has a distal end portion. The tracking device is mechanically coupled to the distal end portion of the interventional medical device. The tracking device includes a plurality of tracking coils, a wireless transmitter, and a power supply circuit. The plurality of tracking coils is configured to interact with the electromagnetic locator field to determine a location within an electromagnetic locator field volume and to generate tracking data. The wireless transmitter is configured to transmit the tracking data from the tracking device of the interventional medical device to the wireless receiver of the ultrasound probe. The power supply circuit is configured to supply electrical power to the wireless transmitter of the tracking device.

The invention, in still another form, is directed to an interventional medical device for use in conjunction with an ultrasound probe. The interventional medical device includes an elongate body having a distal end portion, and a tracking device mechanically coupled to the distal end portion of the interventional medical device. The tracking device includes a plurality of tracking coils, a wireless transmitter, and a power supply circuit. The plurality of tracking coils is configured to determine a location of the tracking device within an electromagnetic locator field volume and to generate tracking data. The wireless transmitter is configured to transmit the tracking data from the tracking device to the ultrasound probe. The power supply circuit is configured to supply electrical power to the wireless transmitter of the tracking device.

An advantage of the present invention is that the electromagnetic locator field volume moves in unison with the ultrasound field-of-view volume, such that correlation between the electromagnetic locator field volume and the ultrasound field-of-view volume is simplified.

Another advantage is that an external electromagnetic locator field generator separate from the ultrasound probe is not required, thus reducing equipment space in the procedure room by reducing the number of free-standing components and connections.

Still another advantage is that, in some embodiments, tracking data is wirelessly transferred from the interventional medical device to the ultrasound probe, such that it is not necessary for the interventional medical device to be physically and/or electrically connected (e.g., tethered) to the ultrasound imaging system in order to facilitate tracking of the location of the interventional medical device.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a graphical depiction of an ultrasound imaging system in accordance with the present invention.

FIG. 2A is a graphical depiction of an electromagnetic locator field volume associated with the ultrasound probe of the ultrasound imaging system of FIG. 1.

FIG. 2B is a graphical depiction of an ultrasound field-of-view volume associated with the ultrasound probe of the ultrasound imaging system of FIG. 1.

Corresponding reference characters indicate corresponding parts throughout the several views. The exemplifications set out herein illustrate embodiments of the invention, and such exemplifications are not to be construed as limiting the scope of the invention in any manner.

DESCRIPTION OF EMBODIMENTS

Figure 3A:
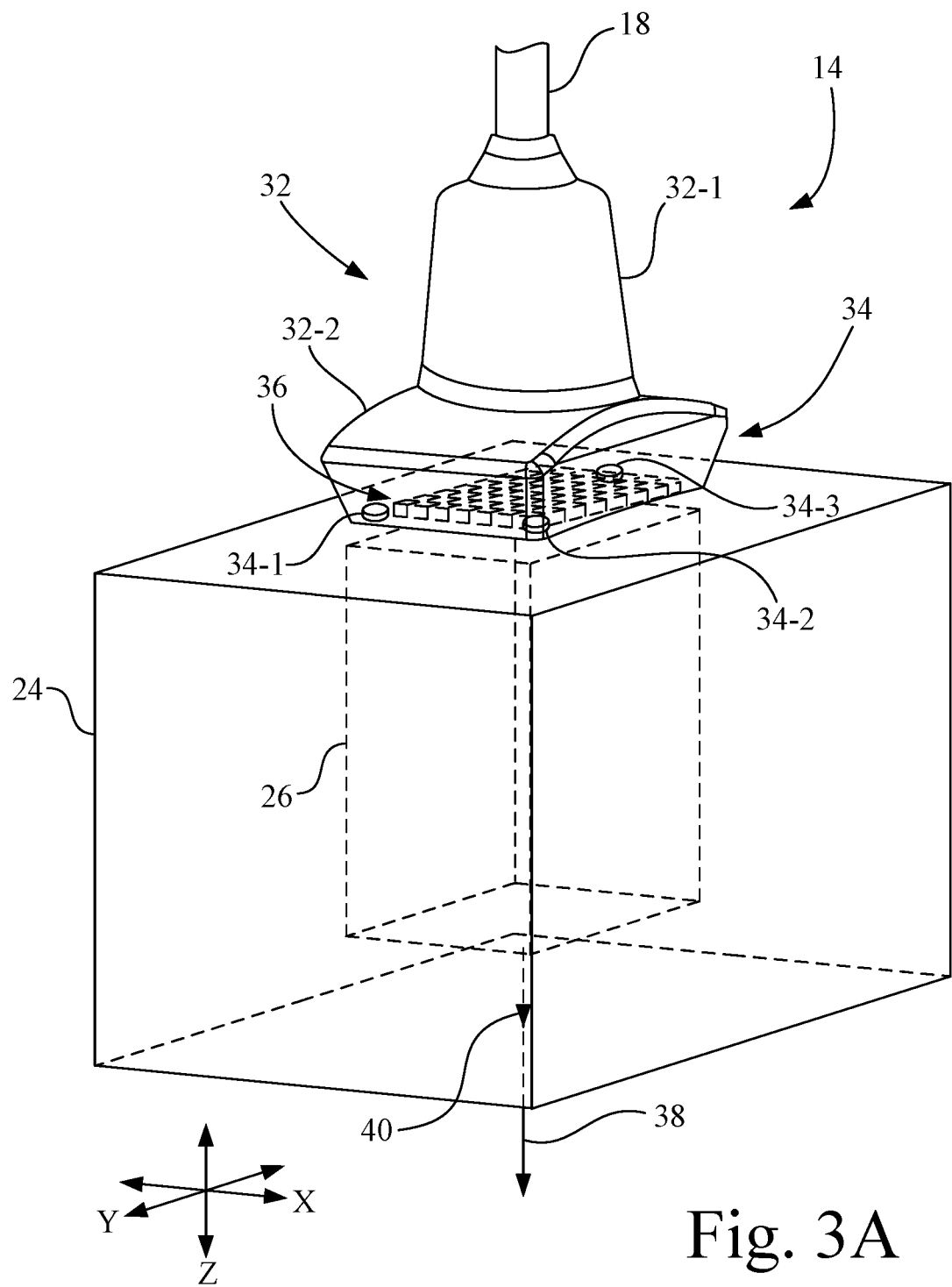
FIG. 3A is a perspective view of the ultrasound probe of the ultrasound imaging system of FIG. 1, in relation to the electromagnetic locator field volume generated by the electromagnetic coils of the ultrasound probe and the ultrasound field-of-view volume generated by the ultrasound transducer array of the ultrasound probe.
Figure 3B:
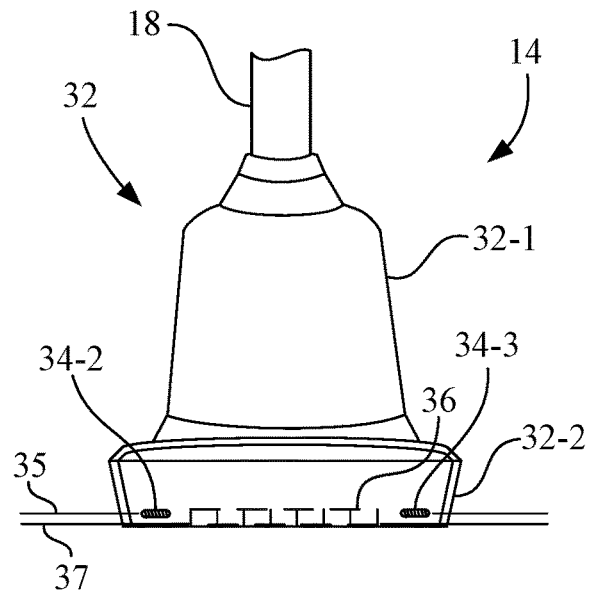
FIG. 3B is a side view of the ultrasound probe of FIG. 3A, with the electromagnetic coils arranged along a plane that is parallel to the planar extents of the ultrasound transducer array.

Referring now to the drawings, and more particularly to FIG. 1, there is shown an ultrasound imaging system 10 in accordance with the present invention. Ultrasound imaging system 10 includes an ultrasound console 12, an ultrasound probe 14 (handheld), and an interventional medical device 16. Typically, interventional medical device 16 will be in the form of a disposable device (i.e., for use with a single patient). Interventional medical device 16 is an intrusive device, such as a guide wire, sheath, angioplasty balloon, catheter, or needle, which is configured to be inserted into the tissue, vessel, or cavity of a patient.

Ultrasound imaging system 10 is configured to direct the user, i.e., clinician, to position ultrasound probe 14 relative to interventional medical device 16. Ultrasound probe 14 is communicatively coupled to ultrasound console 12 by a flexible communication cable 18, e.g., an electrical cable. Interventional medical device 16 is communicatively coupled to ultrasound console 12 via a flexible communication cable 20, e.g., and electrical cable.

Interventional medical device 16 has a distal end portion 16-1 that includes a tracking element 22, which is used in identifying the location of the distal end portion 16-1 of interventional medical device 16 relative to the patient and ultrasound probe 14.

Referring also to FIGS. 2A and 2B, in accordance with one aspect of the present invention, ultrasound probe 14 is configured to generate an electromagnetic (EM) locator field having an electromagnetic (EM) locator field volume 24 and is configured to generate ultrasound imaging data in an ultrasound field-of-view volume 26. Stated differently, ultrasound probe 14 is configured to generate both of the electromagnetic (EM) locator field volume 24 and the ultrasound field-of-view volume 26.

Each of the EM locator field volume 24 and ultrasound field-of-view volume 26 is a three-dimensional (3D) volume. Preferably, the EM locator field volume 24 is greater than or equal to the ultrasound field-of-view volume 26, such that an entirety of the ultrasound field-of-view volume 26 is located within the EM locator field volume 24. For ease of illustration, each of the EM locator field volume 24 and ultrasound field-of-view volume 26 is represented as a rectangular (cubic) volume, but those skilled in the art will recognize that the respective field volumes of the EM locator field volume 24 and ultrasound field-of-view volume 26 may have other shapes, such as for example, trapezoidal, spherical, conical, or irregular volumes.

Referring again to FIG. 1, tracking element 22 of interventional medical device 16 is configured to generate tip location data defining a plurality of degrees of freedom (e.g., X-axis, Y-axis, Z-axis) based on the EM locator field volume 24 generated by ultrasound probe 14. In the present embodiment, tracking element 22 may include multiple sensor coils that interact with the EM locator field volume 24. In the present embodiment, tracking element 22 is mounted at distal end portion 16-1 of interventional medical device 16, e.g., in a range of zero to 2 centimeters (cm) from the distal tip of interventional medical device 16, with the extent of distal end portion 16-1 being 3 cm or less from the distal end of interventional medical device 16. Those skilled in the art will recognize, however, that the exact location of the placement of tracking element 22 on interventional medical device 16 will depend on the portion of interventional medical device 16 that is to be tracked by ultrasound imaging system 10. Tracking element 22 allows the location of interventional medical device 16 to be known relative to ultrasound probe 14, such that ultrasound probe 14 may be moved to a location such that distal end portion 16-1 of interventional medical device 16 appears in an ultrasound image generated from the ultrasound data associated with the ultrasound field-of-view volume 26.

In some applications, it may be preferred to have the volume of EM locator field volume 24 to be much larger than the volume of the ultrasound field-of-view volume 26 (e.g., 2 to 5 times), i.e., wherein the ultrasound imaging volume is a volumetric subset of the EM field volume, so that tracking element 22 of interventional medical device 16 will be sensed and its location relative to the current position of ultrasound probe 14 determined prior to tracking element 22 reaching the ultrasound field-of-view volume 26 of ultrasound probe 14. As such, ultrasound imaging system 10 will generate visual, tactile, and/or aural feedback to guide the user to properly position ultrasound probe 14, such that the distal end portion 16-1 of interventional medical device 16 is included in the ultrasound image generated from data associated with ultrasound field-of-view volume 26. This will ensure that the user is aware of the location of ultrasound probe 14 relative to the tracking element 22 of interventional medical device 16, so as to facilitate a manual positioning of ultrasound probe 14 such that distal end portion 16-1 of interventional medical device 16 having tracking element 22 is within the ultrasound field-of-view volume 26 of ultrasound probe 14.

The visual and/or aural feedback may be presented to the user by ultrasound console 12 or ultrasound probe 14, e.g., in the form of directional arrows and/or voice directional commands. The tactile feedback may be in the form of a vibration that is transferred to ultrasound probe 14 when the distal end portion 16-1 of interventional medical device 16 enters the different volumes due to the movement, i.e., positioning, of ultrasound probe 14. For example, one pulse of vibration may be generated when tracking element 22 at distal end portion 16-1 of interventional medical device 16 enters the EM locator field volume 24, and two pulses of vibration may be generated when tracking element 22 at distal end portion 16-1 of interventional medical device 16 enters the ultrasound field-of-view volume 26.

During a calibration of ultrasound probe 14, a three-axis origin 28 (0, 0, 0 in Cartesian (X, Y, Z) coordinates) is defined in a central portion of the EM locator field volume 24 and a three-axis origin 30 (0, 0, 0 in Cartesian (X, Y, Z) coordinates) is defined in a central portion of the ultrasound field-of-view volume 26. The three-axis origin 28 of the EM locator field volume 24 may be placed anywhere within the ultrasound field-of-view volume 26, or alternatively, the three-axis origin 30 of the ultrasound field-of-view volume 26 may be placed anywhere within the EM locator field volume 24. However, in the present embodiment, during calibration, it is preferred to position the three-axis origin 30 of the ultrasound field-of-view volume 26 to match, i.e., be coincident with, the three-axis origin 28 of the EM locator field volume 24.

As shown in FIGS. 3A-3D, ultrasound probe 14 includes a probe housing 32 having a handle portion 32-1 and a head portion 32-2. Handle portion 32-1 extends upwardly from the head portion, and is sized and shaped to be grasped by a user. Ultrasound probe 14 further includes both an electromagnetic (EM) locator field generator 34 that is mounted to, e.g., contained within, probe housing 32 for generating EM locator field volume 24 and an ultrasound transducer array 36 that is mounted to, e.g., contained within probe housing 32 for generating the ultrasound field-of-view volume 26. More particularly, in all embodiments, ultrasound transducer array 36 is mounted to head portion 32-2 of ultrasound probe 14.

As used herein, the term "mounted to" refers to an attachment to a structure (e.g., probe housing 32) using a fixing medium, such as one or more of adhesive, weld, clamp, mechanical fastener, frame, or incorporation into the material that forms the structure, e.g., into the plastic of probe housing 32, such as by overmolding the component to be attached into the material (e.g., plastic) forming the structure of the housing.

In the present embodiment, EM locator field generator 34 of ultrasound probe 14 includes multiple electromagnetic (EM) coils, which in the present embodiment are three EM coils individually identified as EM coil 34-1, EM coil 34-2, and EM coil 34-3. In the present embodiment, each of the EM coils 34-1, 34-2, 34-3 is mounted to head portion 32-2 of ultrasound probe 14, such as by overmolding the EM coils into the material (e.g., plastic) forming the structure of head portion 32-2 of probe housing 32.

Figure 5:
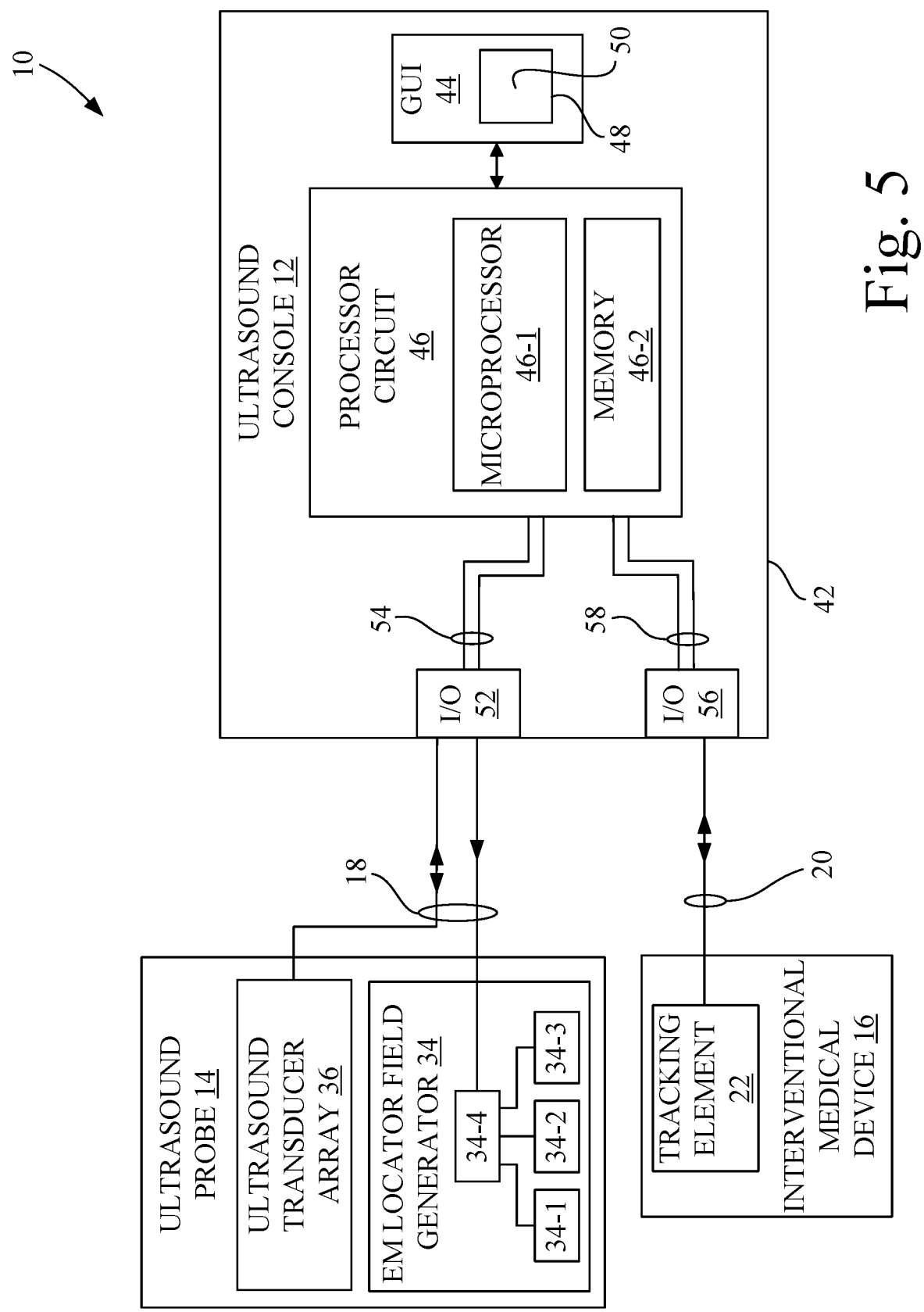
FIG. 5 is a block diagram of the ultrasound imaging system of FIG. 1.

Referring also to FIG. 5, EM locator field generator 34 includes a current driver circuit 34-4 which generates current to be supplied to each of the EM coils in ultrasound probe 14. Current driver circuit 34-4 may be incorporated into ultrasound probe 14, or alternatively, may be remote from ultrasound probe 14.

A field strength generated by EM locator field generator 34 of ultrasound probe 14 defines the size of the EM locator field volume 24, i.e., the detection volume of ultrasound probe 14. In particular, the size of EM locator field volume 24 is dependent upon the amount of current supplied to each of the EM coils of ultrasound probe 14. The volume, shape, and EM field strength of EM locator field volume 24 may be varied by selectively varying the current to one or more of the EM coils of ultrasound probe 14. For example, the volume of EM locator field volume 24 may be increased by increasing the current to the EM coils of ultrasound probe 14, or may be decreased by decreasing the current to the EM coils of ultrasound probe 14.

Figure 3C:
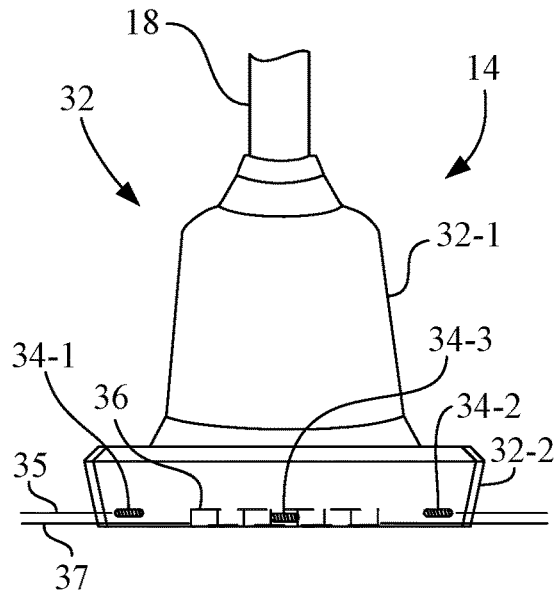
FIG. 3C is a front view of the ultrasound probe of FIG. 3A.
Figure 3D:
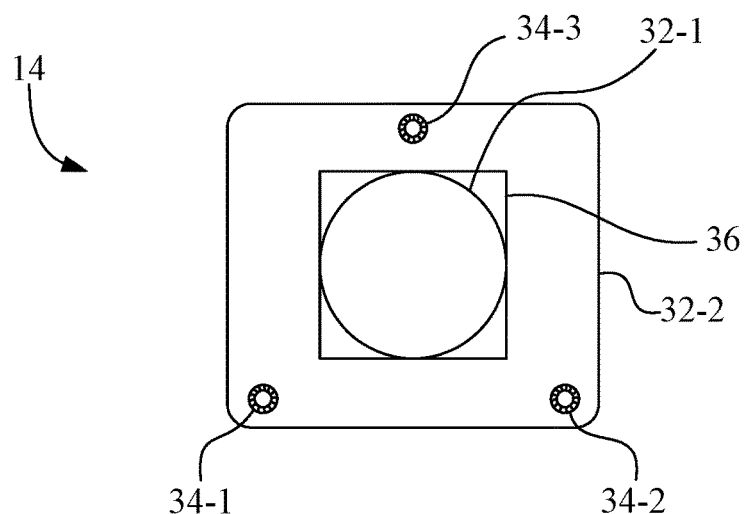
FIG. 3D is a top view of the ultrasound probe of FIG. 3A, showing the electromagnetic coils arranged along the plane in a triangular pattern.

Referring again to FIGS. 3A-3D, in the present embodiment, the three EM coils 34-1, 34-2, 34-3 are arranged in a triangle (e.g., an equilateral triangle) having a centroid. The centroid of the triangle arrangement of three EM coils 34-1, 34-2, 34-3 defines a Z-axis 38 of the EM locator field volume 24. Also, the centroid of the triangular arrangement of the EM coils is centered on a Z-axis 40 of ultrasound transducer array 36 of ultrasound probe 14. Referring to FIG. 3C, an EM coil plane 35 of the triangle of EM coil 34-1, EM coil 34-2, and EM coil 34-3 is parallel to, or coincident with, the X-Y plane 37 (i.e., the planar extents) of ultrasound transducer array 36. EM coils 34-1, 34-2, 34-3 and ultrasound transducer array 36 are arranged to facilitate an entirety of the ultrasound field-of-view volume 26 being located within the EM locator field volume 24.

The Z-axis 40 of ultrasound transducer array 36 is defined at a centroid of ultrasound transducer array 36, and is also the Z-axis 40 of the ultrasound field-of-view volume 26. In a preferred embodiment, Z-axis 40 of ultrasound field-of-view volume 26 and ultrasound transducer array 36 is coaxial with the Z-axis 38 of the EM locator field volume 24, such that each of three-axis origin 28 of the EM locator field volume 24 and three-axis origin 30 of the ultrasound field-of-view volume 26 lies on the Z-axis 40 of ultrasound transducer array 36 of ultrasound probe 14.

EM coil 34-1, EM coil 34-2, and EM coil 34-3 collectively provide three degrees of freedom (three directions of location) within the EM locator field volume 24 and ultrasound field-of-view volume 26 of ultrasound probe 14. Additional degrees of freedom may be established with the addition of a corresponding number of additional EM coils in ultrasound probe 14.

In the present embodiment, it is preferred that the Z-axis 38 of the EM locator field volume 24 (at the centroid of the triangle arrangement of the three EM coils 34-1, 34-2, 34-3) be axially aligned with the Z-axis 40 of the ultrasound field-of-view volume 26, and that the respective origins be aligned such that the three-axis origin 28 of the EM locator field volume 24 matches, i.e., is coincident with, that of the three-axis origin 30 of the ultrasound field-of-view volume 26. Accordingly, the EM locator field volume 24 and ultrasound field-of-view volume 26 can be mapped one to one with minimal translation, if any, between one volume and the other volume.

Figures 4A, 4B:
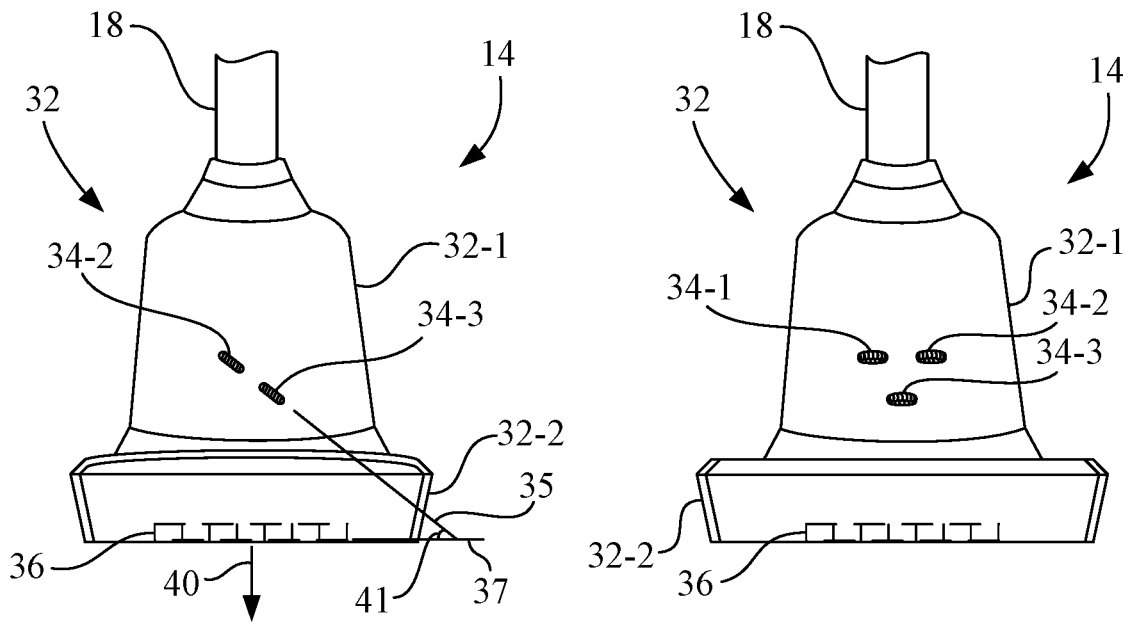
FIG. 4A is a side view of another embodiment of the ultrasound probe of the ultrasound imaging system of FIG. 1, having an alternative configuration of the electromagnetic coils wherein the coils are arranged along a plane that is non-parallel to the planar extents of the ultrasound transducer array.
FIG. 4B is a front view of the ultrasound probe of FIG. 4A.
Figure 4C:
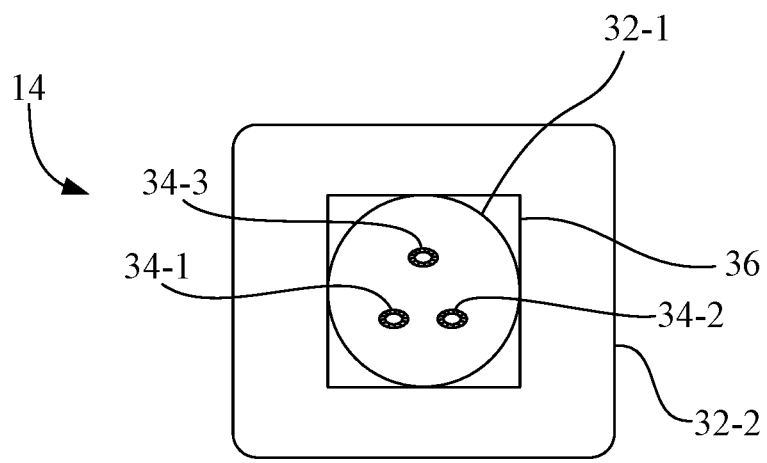
FIG. 4C is a top view of the ultrasound probe of FIG. 4A, showing the electromagnetic coils arranged along the plane in a triangular pattern.

Referring to FIGS. 4A-4C, alternatively, EM locator field generator 34 of ultrasound probe 14 may be located in a handle portion 32-1 of ultrasound probe 14, such that the EM coil plane 35 of the triangle formed by EM coil 34-1, EM coil 34-2, and EM coil 34-3, is arranged at an acute angle with respect to the Z-axis 40 of the ultrasound field-of-view volume 26 of ultrasound probe 14, and thus with the EM coil plane 35 of the triangle of EM coil 34-1, EM coil 34-2, and EM coil 34-3 also arranged at an acute angle 41 with respect to the X-Y plane 37 of ultrasound transducer array 36. Acute angle 41 may be in a range of greater than zero degrees, but less than 45 degrees. EM coils 34-1, 34-2, 34-3 and ultrasound transducer array 36 are arranged to facilitate an entirety of the ultrasound field-of-view volume 26 being located within the EM locator field volume 24.

If the three EM coils 34-1, 34-2, 34-3 are placed at acute angle 41 within handle portion 32-1 of ultrasound probe 14, the field volume of EM locator field volume 24 will be offset from the ultrasound imaging volume of ultrasound field-of-view volume 26 by that angle. To compensate for this angular offset, a translation is calculated between EM locator field volume 24 and the ultrasound field-of-view volume 26 so that the tracking element 22 of interventional medical device 16 will be mapped to, and appear properly within, the ultrasound image extracted from and/or generated in the ultrasound imaging volume of ultrasound field-of-view volume 26. Thus, via compensation, the Z-axis of the electromagnetic locator field volume may be axially aligned with the Z-axis 40 of the ultrasound field-of-view volume 26, and additionally, the respective origins of the EM locator field volume 24 and ultrasound field-of-view volume 26 may be aligned, i.e., coincident with each other.

In the present embodiment, for producing a 3D dataset, ultrasound transducer array 36 of ultrasound probe 14 may be a 2D matrix of piezoelectric elements that are electronically scanned in a sweeping motion. As such, the ultrasound field-of-view volume 26 is comprised of a plurality of sequentially generated ultrasound image slices. Alternatively, ultrasound transducer array 36 of ultrasound probe 14 may be a mechanically movable one-dimensional (1D) linear array of piezoelectric elements that is mechanically scanned to generate a plurality of sequentially generated ultrasound image slices. As a further alternative, if desired, either of the electronically scanned 2D matrix or the mechanically movable one-dimensional (1D) linear transducer array may be configured, e.g., in a non-sweeping mode, to emulate a fixed-position linear array (i.e., fixed with respect to probe housing 32) that generates a single ultrasound image slice (refreshed periodically), in which case the ultrasound field-of-view volume 26 is narrowed to the thickness of the single ultrasound image slice.

Referring again to FIG. 1, ultrasound imaging system 10 is configured to direct the user, i.e., clinician, through visual, tactile, and/or aural feedback to change the location of the ultrasound probe 14 so that tracking element 22 of interventional medical device 16 is within ultrasound field-of-view volume 26, i.e., such that ultrasound transducer array 36 of ultrasound probe 14 is dynamically positioned by the user to image a desired portion, i.e., the distal end portion 16-1 of interventional medical device 16, that corresponds to the location of tracking element 22. The visual and/or aural feedback may be presented to the user by ultrasound console 12 or ultrasound probe 14, e.g., in the form of directional arrows and/or voice directional commands. The tactile feedback may be in the form of vibration pulses that are transferred to probe housing 32 of ultrasound probe 14 when tracking element 22 at distal end portion 16-1 of interventional medical device 16 enters the different volumes (i.e., EM locator field volume 24 and ultrasound field-of-view volume 26) due to the movement, i.e., positioning, of ultrasound probe 14.

In the present embodiment as depicted in FIG. 1, ultrasound console 12 includes a console housing 42, to which a graphical user interface (GUI) 44 and a processor circuit 46 is attached. Graphical user interface 44 may be in the form of a touch-screen 48 having a display screen 50. Graphical user interface 44 is used in displaying information to the user, and accommodates user input via touch-screen 48. For example, touch-screen 48 is configured to display an ultrasound image formed from two-dimensional ultrasound slice data provided by ultrasound probe 14 that includes distal end portion 16-1 of interventional medical device 16 having tracking element 22 within the 3D imaging volume of ultrasound field-of-view volume 26, and to display prompts intended to guide the user in the correct positioning of the ultrasound probe 14 relative to the location of tracking element 22, i.e., the region of interest in the patient. In addition, display screen 50 may be configured as a standard 2D display, or optionally, may be configured as a 3D display. For example, the 3D dataset captured by ultrasound imaging system 10 may be presented to the user via an autostereoscopic or other display method that presents a 3D image to the user.

Referring also to the block diagram of FIG. 5, processor circuit 46 is an electrical circuit that has data processing capability and command generating capability. In the present embodiment, processor circuit 46 has a microprocessor 46-1 and associated non-transitory electronic memory 46-2. Microprocessor 46-1 and associated non-transitory electronic memory 46-2 are commercially available components, as will be recognized by one skilled in the art. Microprocessor 46-1 may be in the form of a single microprocessor, or two or more parallel microprocessors, as is known in the art. Non-transitory electronic memory 46-2 may include multiple types of digital data memory, such as random access memory (RAM), non-volatile RAM (NVRAM), read only memory (ROM), and/or electrically erasable programmable read-only memory (EEPROM). Non-transitory electronic memory 46-2 may further include mass data storage in one or more of the electronic memory forms described above, or on a computer hard drive or optical disk. Alternatively, processor circuit 46 may be assembled as one or more Application Specific Integrated Circuits (ASIC).

Processor circuit 46 processes program instructions received from a program source, such as software or firmware, to which processor circuit 46 has electronic access. More particularly, processor circuit 46 is configured to execute program instructions to process tip location data received from interventional medical device 16 to correlate the current position of the tracking element 22 at the distal end portion 16-1 of interventional medical device 16 with the three-axis origin 28 of the EM locator field volume 24 and the three-axis origin 30 of the ultrasound field-of-view volume 26 of ultrasound probe 14.

Processor circuit 46 of ultrasound console 12 is communicatively coupled to ultrasound probe 14 via an ultrasound probe input/output (I/O) interface circuit 52, an internal bus structure 54, and communication cable 18. As used herein, the term "communicatively coupled" means connected for communication over a communication medium, wherein the communication medium may be a direct wired connection having electrical conductors and/or printed circuit electrical conduction paths, or a wireless connection, and may be an indirect wired or wireless connection having intervening electrical circuits, such as amplifiers or repeaters.

In the present embodiment, ultrasound probe I/O interface circuit 52 is connected to communication cable 18, which in turn is connected to both EM locator field generator 34 of ultrasound probe 14 and ultrasound transducer array 36 of ultrasound probe 14. Also, ultrasound probe I/O interface circuit 52 is connected to processor circuit 46 via internal bus structure 54. Internal bus structure 54 may be formed, for example, as metallic traces on a printed circuit board, or may be a wired cable connection.

Processor circuit 46 is configured to generate and supply control signals to current driver circuit 34-4 of EM locator field generator 34, so as to selectively control the amount of current supplied to each of the EM coils (e.g., EM coils 34-1, 34-2, 34-3) incorporated into ultrasound probe 14. The volume and/or shape of EM locator field volume 24 may be varied by selectively varying the current to one or more of the EM coils of ultrasound probe 14. Alternatively, it is contemplated that current driver circuit 34-4 may be incorporated into ultrasound console 12, if desired.

Ultrasound transducer array 36 supplies two-dimensional ultrasound slice data to processor circuit 46 via communication cable 18. Automatically, or alternatively based on a user input at graphical user interface 44, processor circuit 46 executes program instructions to store the two-dimensional ultrasound slice data in mass storage provided in non-transitory electronic memory 46-2.

Processor circuit 46 includes circuitry, or alternatively executes program instructions, to convert the two-dimensional ultrasound data supplied by ultrasound transducer array 36 to a form for viewing as one or more two-dimensional ultrasound image slices, or a 3D imaging volume, on display screen 50 of graphical user interface 44. Once that ultrasound probe 14 is guided to the proper location relative to interventional medical device 16, the viewed image will include interventional medical device 16 having tracking element 22 located in a portion of the body of a patient, e.g., a blood vessel, body cavity.

Processor circuit 46 is communicatively coupled to a device input/output (I/O) interface circuit 56 via an internal bus structure 58 and communication cable 20. Internal bus structure 58 may be formed, for example, as metallic traces on a printed circuit board, or may be a wired cable connection. In the present embodiment, device I/O interface circuit 56 is configured to connect to flexible communication cable 20, which in turn is connected to tracking element 22 of interventional medical device 16. Tracking element 22 supplies device location data to processor circuit 46 via communication cable 20 and internal bus structure 58 to facilitate the determination of the location of interventional medical device 16 within the detection volume of EM locator field volume 24 of ultrasound probe 14, wherein in the present embodiment, the EM locator field volume 24 of ultrasound probe 14 is larger than the three-dimensional ultrasound field-of-view volume 26 of ultrasound probe 14.

Based on the device location data received from interventional medical device 16 relative to the reference location of the EM locator field volume 24 generated by ultrasound probe 14, processor circuit 46 executes program instructions to generate visual and/or aural feedback to guide the user to properly position ultrasound probe 14, such that the distal end portion 16-1 of interventional medical device 16 is included in the ultrasound image generated from data associated with ultrasound field-of-view volume 26.

Figure 6:
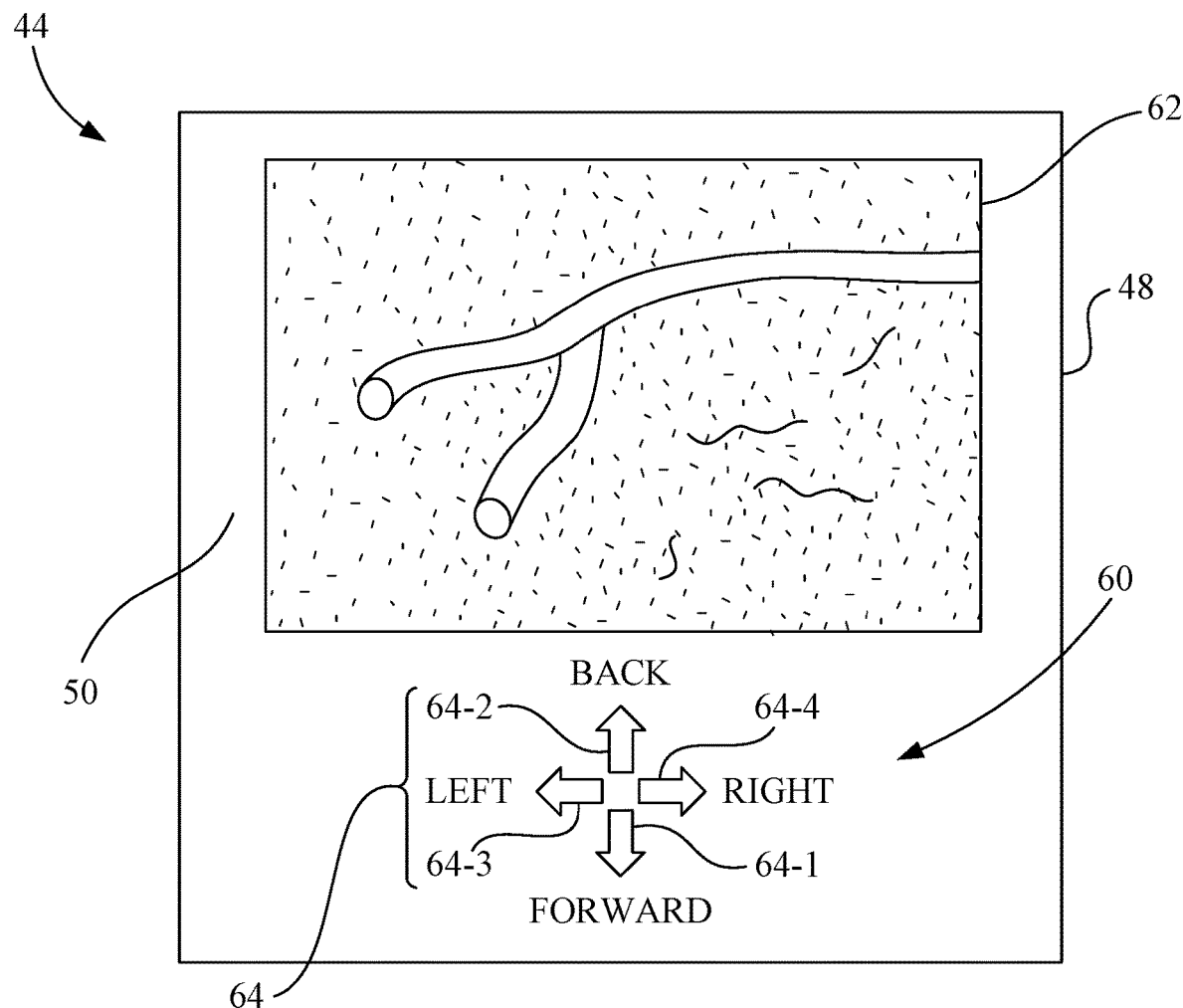
FIG. 6 is graphical depiction of a graphical user interface having both a directional indicator for guiding a user and a current ultrasound image displayed on the display screen.

For example, as illustrated in FIG. 6, a directional indicator 60 may be generated at the graphical user interface 44, along with a current ultrasound image 62, such as by selectively illuminating one or two of a plurality of directional indicator arrows 64 (e.g., Forward 64-1, Back 64-2, Left 64-3, Right 64-4) on display screen 50, which point in the direction in which the user needs to move ultrasound probe 14. Alternatively, directional indicator 60, e.g., illuminated directional arrows 64, may be located directly on probe housing 32 of ultrasound probe 14.

Figure 7A:
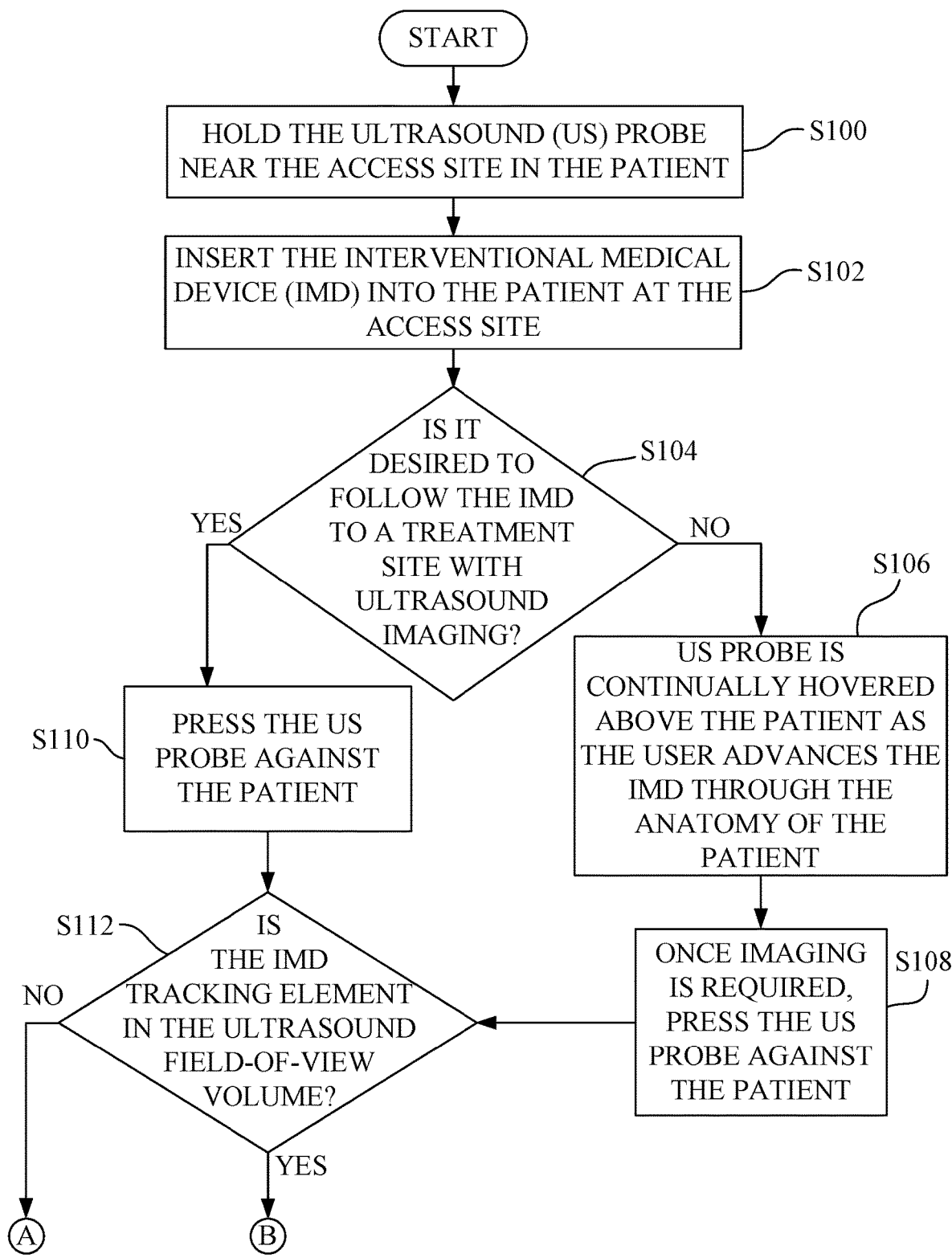
FIGS. 7A and 7B together form a flowchart of a method of use of the ultrasound imaging system of FIGS. 1 and 5, in accordance with an aspect of the present invention.
Figure 7B:
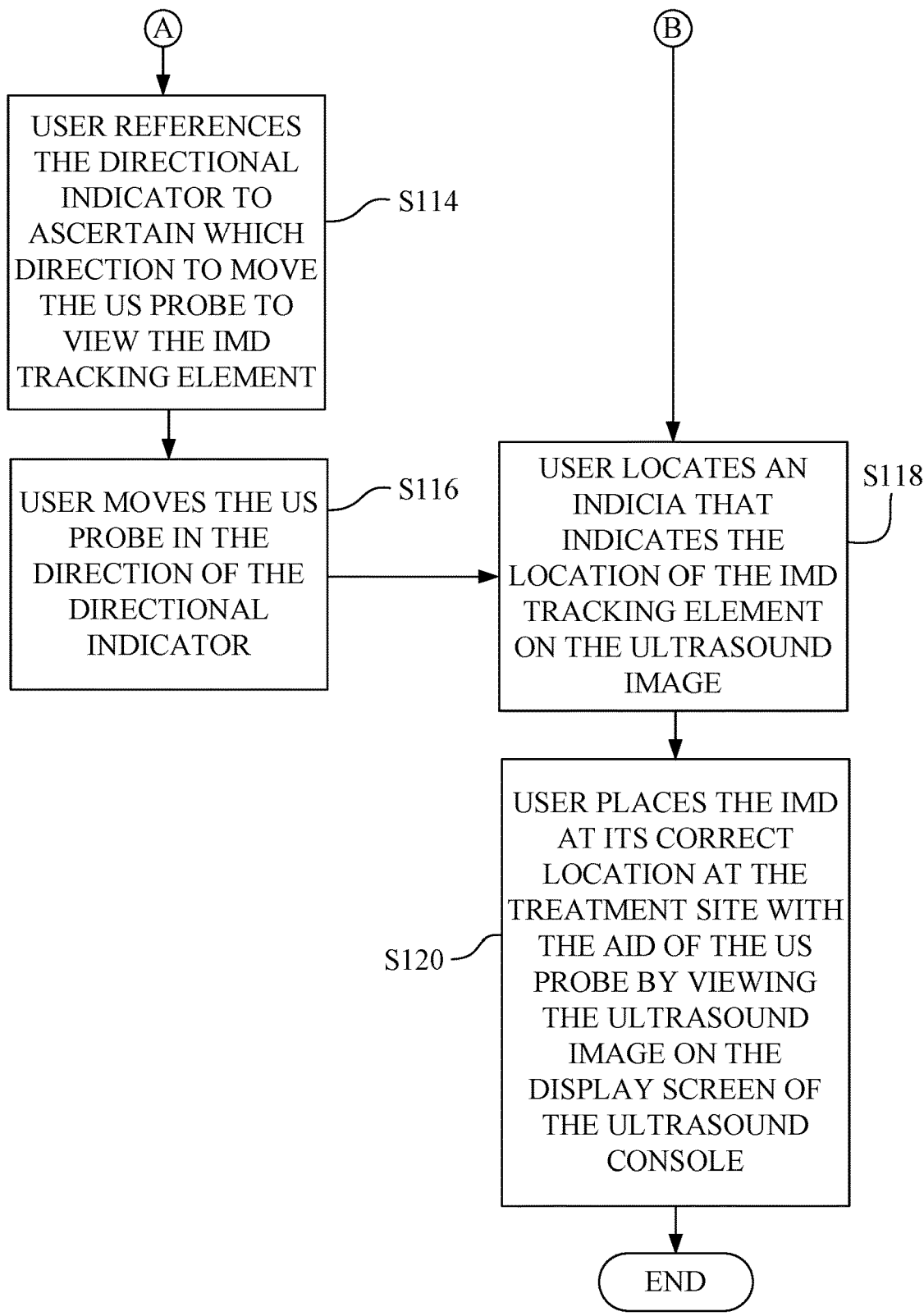

FIGS. 7A and 7B together form a flowchart of a method of use of the ultrasound imaging system 10, in accordance with an aspect of the present invention.

At step S100, the user holds ultrasound probe 14 near an access site in the patient. The access site may be an incision, or may be a lumen opening of a catheter previously inserted into the patient.

At step S102, interventional medical device 16 is inserted into the patient at the access site.

At step S104, it is determined whether it is desired to follow interventional medical device 16 to a treatment site within the patient.

If the determination at step S104 is NO, then at step S106, ultrasound probe 14 is continually hovered above the patient as the user advances interventional medical device 16 to the treatment site. At step S108, when ultrasound imaging is required, then ultrasound probe 14 is pressed against the patient.

If the determination at step S104 is YES, then at step S110, ultrasound probe 14 is pressed against the patient.

At the conclusion of either of steps S108 and S110, then at step S112, it is determined whether tracking element 22 of interventional medical device 16 is in the ultrasound field-of-view volume 26. All (full 3D image), or a portion (2D slice or 3D portion), of the ultrasound field-of-view volume is displayed in the ultrasound image presented at display screen 50.

If the determination at step S112 is NO, then at step S114, the user references the directional indicator 60 (see FIG. 6) to ascertain which direction to move ultrasound probe 14 to locate and view tracking element 22 of interventional medical device 16. Then, at step S116, the user moves ultrasound probe 14 in the direction indicated by directional indicator 60.

At the conclusion of step S116, or if the determination at step S112 is YES, then at step S118 the user locates on the displayed ultrasound image an indicia, e.g., a dot, that indicates the location to tracking element 22 of interventional medical device 16.

At step S120, the user places, i.e., positions, the interventional medical device 16 at the correct location at the treatment site with the aid of the ultrasound image generated by ultrasound probe 14, by viewing the ultrasound image on display screen 50 of ultrasound console 12.

The following items also relate to the invention:

In one form, the invention relates to an ultrasound probe for use in an ultrasound imaging system comprising a probe housing; an ultrasound transducer array mounted to the probe housing, the ultrasound transducer array configured to generate an ultrasound field-of-view volume; and an electromagnetic locator field generator mounted to the probe housing, the electromagnetic locator field generator configured to generate an electromagnetic locator field volume. Optionally, the electromagnetic locator field generator has a plurality of electromagnetic coils. The plurality of electromagnetic coils may be incorporated into a material that forms the probe housing. In one embodiment, the ultrasound probe housing may include a handle portion and a head portion, wherein each of the ultrasound transducer array and the electromagnetic locator field generator is located in the head portion. In another embodiment, the ultrasound probe housing may include a handle portion and a head portion, wherein the ultrasound transducer array is located in the head portion and the electromagnetic locator field generator is located in the handle portion. In each embodiment, a first Z-axis of the electromagnetic locator field volume may be axially aligned with a second Z-axis of the ultrasound field-of-view volume. Additionally or alternatively, a first three-axis origin may be defined in a central portion of the electromagnetic locator field volume and a second three-axis origin may be defined in the ultrasound field-of-view volume, wherein the second three-axis origin of the ultrasound field-of-view volume is positioned to be coincident with the first three-axis origin of the electromagnetic locator field volume.

In another form, the invention relates to an ultrasound probe for use in an ultrasound imaging system comprising a probe housing; an ultrasound transducer array mounted to the probe housing, the ultrasound transducer array configured to generate an ultrasound field-of-view volume; and a plurality of electromagnetic coils mounted to the probe housing, the plurality of electromagnetic coils configured to generate an electromagnetic locator field volume, wherein the ultrasound transducer array and the plurality of electromagnetic coils are arranged such that an entirety of the ultrasound field-of-view volume is located within the electromagnetic locator field volume. The plurality of electromagnetic coils may be three electromagnetic coils. In one embodiment, the three electromagnetic coils may be arranged in a triangle arrangement that defines a plane that is parallel to a plane of the ultrasound transducer array. A first Z-axis of the electromagnetic locator field volume may be axially aligned with a second Z-axis of the ultrasound field-of-view volume. In addition or alternatively, a first three-axis origin may be defined in a central portion of the electromagnetic locator field volume and a second three-axis origin may be defined in a central portion of the ultrasound field-of-view volume, wherein the second three-axis origin of the ultrasound field-of-view volume is positioned to be coincident with the first three-axis origin of the electromagnetic locator field volume. In another embodiment, the plurality of electromagnetic coils may be arranged in a triangle arrangement that defines a plane that is non-parallel to a plane of the ultrasound transducer array. In each of the embodiments, each of the plurality of electromagnetic coils may be incorporated into a material that forms the probe housing.

In another form, the invention relates to an ultrasound imaging system comprising an ultrasound console having a graphical user interface; an interventional medical device communicatively coupled to the ultrasound console, the interventional medical device having a tracking element; and an ultrasound probe communicatively coupled to the ultrasound console. The ultrasound probe includes: a probe housing; an ultrasound transducer array mounted to the probe housing, the ultrasound transducer array configured to generate an ultrasound field-of-view volume; and an electromagnetic locator field generator that includes a plurality of electromagnetic coils that are mounted to the probe housing of the ultrasound probe, the plurality of electromagnetic coils configured to generate an electromagnetic locator field volume for identifying a location of the tracking element of the interventional medical device within the electromagnetic locator field volume. The plurality of electromagnetic coils may be three electromagnetic coils. In one embodiment, the three electromagnetic coils may be arranged in a triangle arrangement that defines a plane that is parallel to a plane of the ultrasound transducer array. In another embodiment, the three electromagnetic coils may be arranged in a triangle arrangement that defines a plane that is non-parallel to a plane of the ultrasound transducer array. In each embodiment, the ultrasound probe housing may include a handle portion and a head portion, wherein each of the ultrasound transducer array and the plurality of electromagnetic coils is located in the head portion. Alternatively, the ultrasound probe housing may include a handle portion and a head portion, wherein the ultrasound transducer array is located in the head portion and the plurality of electromagnetic coils is located in the handle portion. In each embodiment, the electromagnetic locator field generator may include a current driver circuit electrically coupled to each of the plurality of electromagnetic coils. A first Z-axis of the electromagnetic locator field volume may be axially aligned with a second Z-axis of the ultrasound field-of-view volume. A first three-axis origin may be defined in a central portion of the electromagnetic locator field volume and a second three-axis origin may be defined in the ultrasound field-of-view volume, wherein the second three-axis origin of the ultrasound field-of-view volume is coincident with the first three-axis origin of the electromagnetic locator field volume.

Optionally, the tracking element is configured to interact with the electromagnetic locator field volume to facilitate determining a location of the interventional medical device in the electromagnetic locator field volume and the ultrasound field-of-view volume. The tracking element may be located at a distal end portion of the interventional medical device, and the tracking element may be configured to interact with the electromagnetic locator field volume to generate tip location data for identifying a location of the interventional medical device within the electromagnetic locator field volume. The ultrasound console may include a processor circuit configured to execute program instructions to process the tip location data received from the tracking element of the interventional medical device to correlate a current position of the tracking element with a first origin of the electromagnetic locator field volume of the ultrasound probe and a second origin of the ultrasound field-of-view volume of the ultrasound probe.

Figure 8:
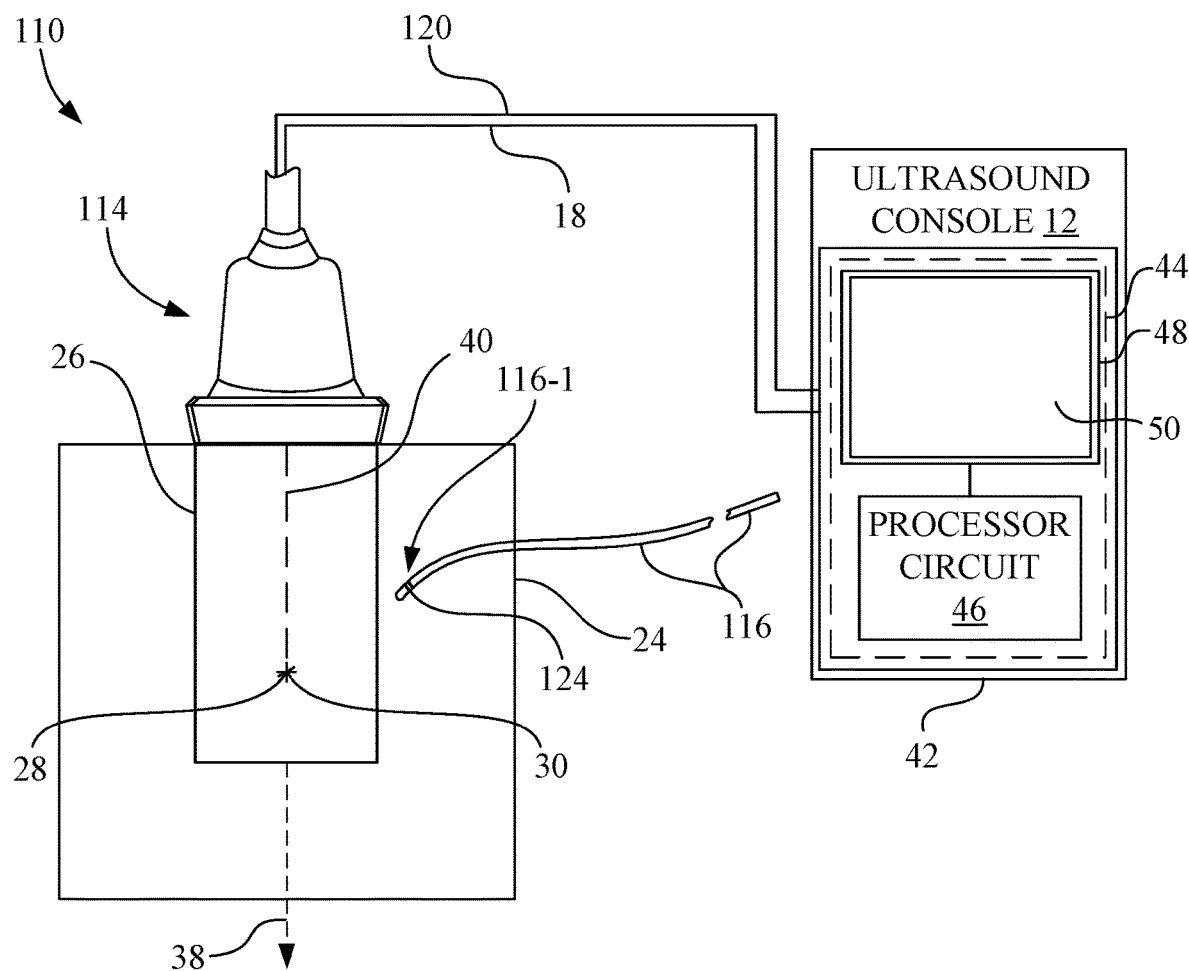
FIG. 8 is a graphical depiction of an ultrasound imaging system in accordance with another embodiment of the present invention, configured to support wireless transmission of tracking data from the interventional medical device to the ultrasound probe.

Referring now to FIG. 8, there is shown a graphical depiction of an ultrasound imaging system 110 in accordance with another embodiment of the present invention. Also, in FIG. 9, there is shown a block diagram of ultrasound imaging system 110.

Ultrasound imaging system 110 is a variation of ultrasound imaging system 10 of FIGS. 1-7B, wherein each of ultrasound probe 14 and interventional medical device 16 of the embodiment of FIGS. 1-7B is modified to form an ultrasound probe 114 and an interventional medical device 116, respectively. As between the description of the ultrasound imaging system 10 of FIGS. 1-7B and the description of ultrasound imaging system 110 that follows, corresponding reference characters indicate corresponding parts in both structure and function, and for brevity, the full descriptions of the corresponding parts will not be repeated.

Ultrasound probe 114 and interventional medical device 116 are configured to support wireless transmission of tracking data from interventional medical device 116 to ultrasound probe 114, wherein the tracking data received by ultrasound probe 114 is supplied to ultrasound console 12 via a communication cable 120, e.g., a flexible multi-wire electrical cable.

Figure 9:
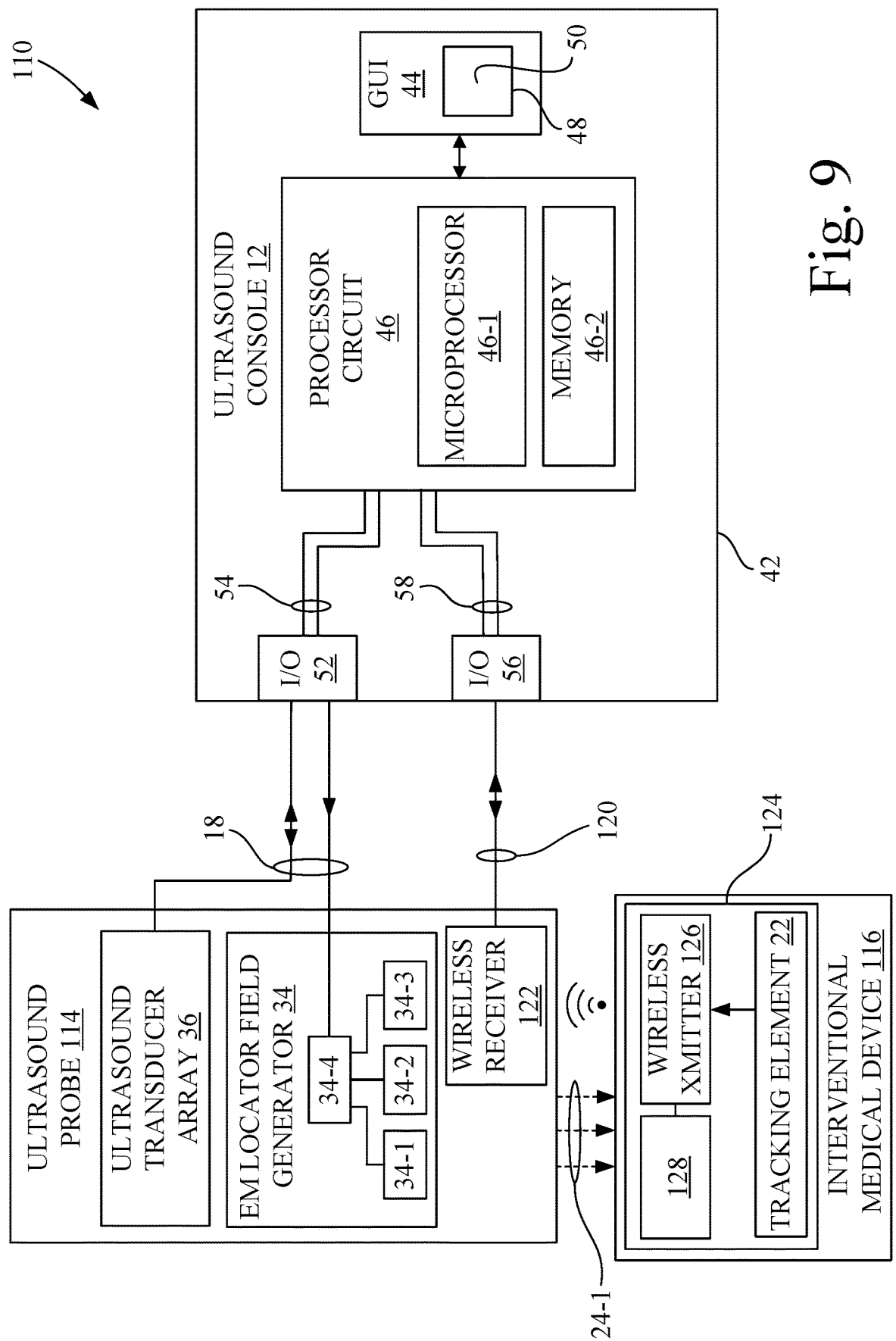
FIG. 9 is a block diagram of the ultrasound imaging system of FIG. 8.

Referring to FIG. 9, ultrasound probe 114 includes ultrasound transducer array 36 and EM locator field generator 34 having, for example, EM coil 34-1, EM coil 34-2, and EM coil 34-3, which operate as described above, which generate an electromagnetic locator field 24-1 to produce the EM locator field volume 24 (see also FIG. 8). Ultrasound probe 114 further includes a wireless receiver 122. In the present embodiment, wireless receiver 122 of ultrasound probe 114 is communicatively coupled to ultrasound console 12 via communication cable 120. More particularly, as shown in FIG. 9, wireless receiver 122 of ultrasound probe 114 is connected to communication cable 120, and the opposite end of communication cable 120 is connected to device I/O interface circuit 56 of ultrasound console 12. Thus, in the present embodiment, processor circuit 46 of ultrasound console 12 is communicatively coupled to wireless receiver 122 of ultrasound probe 114 via device I/O interface circuit 56, internal bus structure 58, and communication cable 120, so as to process the tracking data generated by, and received from, interventional medical device 116.

Referring to FIGS. 8 and 9, interventional medical device 116 may be, for example, in the form of an elongate disposable device (i.e., for use with a single patient). Interventional medical device 116 is an intrusive device, such as for example, a guide wire, sheath, angioplasty balloon, catheter, or needle, which is configured to be inserted into the tissue, vessel, or cavity of a patient. In the present embodiment, interventional medical device 116 has a distal end portion 116-1 that includes a tracking device 124.

Referring to FIG. 9, tracking device 124 includes tracking element 22, a wireless transmitter 126 (abbreviated as xmitter 126 in the drawing), and a power supply circuit 128. Power supply circuit 128 is configured to wirelessly receive energy (e.g., electromagnetic or ultrasonic energy) emitted from ultrasound probe 114, and to convert the received energy into direct current (DC) voltage and current for satisfying the electrical power requirements of wireless transmitter 126.

Each of wireless receiver 122 of ultrasound probe 114 and wireless transmitter 126 of interventional medical device 116 may be, for example, in the form of an inductive coupling circuit, or alternatively, may be in the form of a radio frequency (RF) circuit or an RFID circuit.

Figure 10:
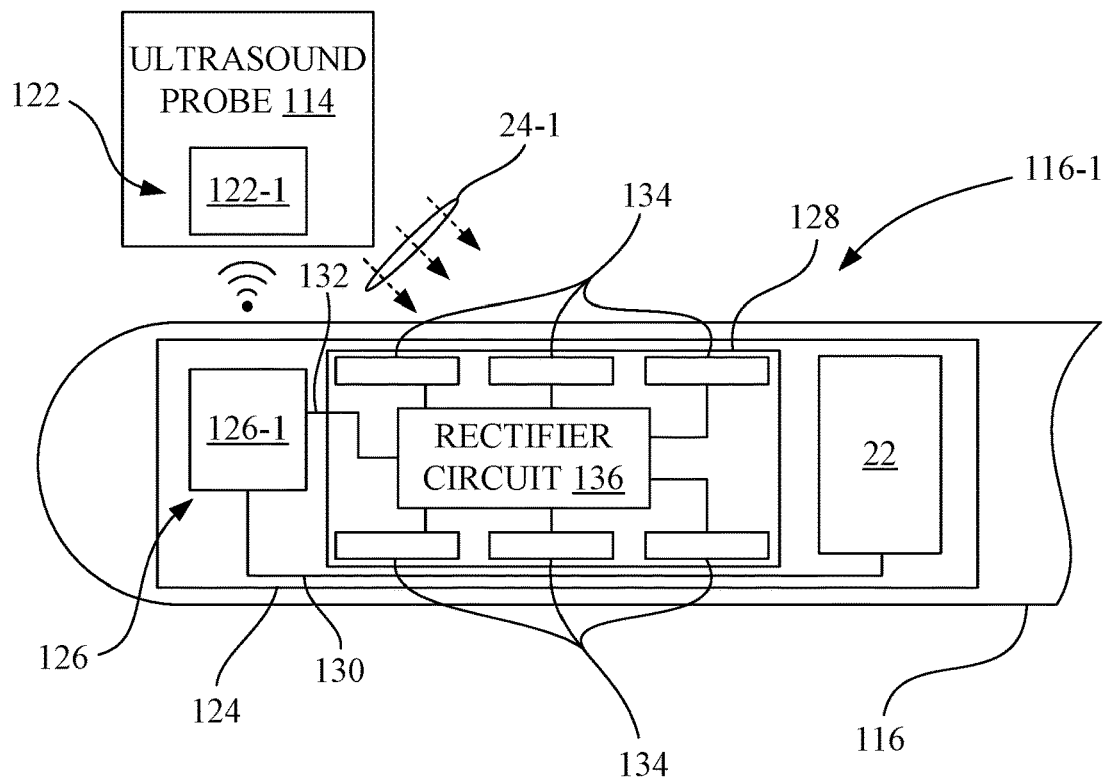
FIG. 10 is a graphical depiction of an enlargement of the distal portion of the interventional medical device having a tracking device that includes a tracking element, a wireless transmitter, and a power supply circuit having a plurality of pickup coils to convert a portion of the electromagnetic locator field received from the ultrasound probe into electrical power for powering the wireless transmitter.

Referring also to FIG. 10, there is shown an enlargement of the distal end portion 116-1 of interventional medical device 116 having tracking device 124, wherein tracking device 124 includes tracking element 22, wireless transmitter 126, and power supply circuit 128. Tracking element 22 is electrically connected to wireless transmitter 126 via an electrical conductor 130, e.g., wires or circuit traces, so as to supply tracking data to wireless transmitter 126 for wireless transfer to wireless receiver 122 of ultrasound probe 114. Power supply circuit 128 is electrically connected to wireless transmitter 126 via an electrical conductor 132, e.g., wires or circuit traces, so as to provide electrical power to wireless transmitter 126.

In the present embodiment, wireless transmitter 126 may be in the form of a near field transmitter circuit 126-1. Near field transmitter circuit 126-1 is electrically connected to tracking element 22 via electrical conductor 130. Likewise, in embodiments wherein wireless transmitter 126 is in the form of near field transmitter circuit 126-1, then wireless receiver 122 of ultrasound probe 114 is in the form of a near field receiver circuit 122-1. Near field receiver circuit 122-1 and near field transmitter circuit 126-1 communicate using a near field communication protocol. Near Field Communication (NFC) is a short-range wireless connectivity standard (Ecma-340, ISO/IEC 18092) that uses magnetic field induction to enable communication between near field transmitter circuit 126-1 and near field receiver circuit 122-1 when near field transmitter circuit 126-1 and near field receiver circuit 122-1 are brought within the communication range, e.g., up to 15 centimeters, of each other.

Alternatively, short range RF communication protocols, such as for example, Bluetooth or Bluetooth low energy (BLE), may accommodate a larger spacing between the wireless receiver 122 and wireless transmitter 126. For example, wireless receiver 122 of ultrasound probe 114 may include a Bluetooth receiver circuit and wireless transmitter 126 may include a Bluetooth transmitter circuit, wherein the Bluetooth receiver circuit and the Bluetooth transmitter circuit communicate using a Bluetooth communication protocol.

As a further alternative, it is contemplated that each of wireless receiver 122 of ultrasound probe 114 and wireless transmitter 126 of interventional medical device 116 may communicate using an RFID circuit and an RFID communication protocol.

Referring again to FIGS. 9 and 10, power supply circuit 128 is electrically connected to near field transmitter circuit 126-1 via electrical conductor 132. In one embodiment, for example, power supply circuit 128 may include a plurality of pickup coils 134 (e.g. pickup coil loops) and a rectifier circuit 136. The pickup coils 134 may be coupled to, e.g., printed on a surface of, or embedded in, interventional medical device 116 at the distal end portion 116-1. Rectifier circuit 136 may include, for example, a full wave bridge rectifier circuit, a power regulation circuit, and appropriate signal filtering, so as to produce a DC power output suitable for satisfying the electrical power requirements of wireless transmitter 126, or more particularly in this example, the electrical power requirements of near field transmitter circuit 126-1.

The plurality of pickup coils 134 at distal end portion 116-1 of interventional medical device 116 are configured to receive the electromagnetic locator field 24-1 from ultrasound probe 114, and to convert a portion of the electromagnetic locator field 24-1 in the EM locator field volume 24 (see also FIG. 8) into electrical power, which in turn is sent to rectifier circuit 136, which in turn produces a DC power output that is supplied to near field transmitter circuit 126-1 of tracking device 124.

Alternatively, the plurality of pickup coils 134 may be a portion of an inductive coupling circuit, which may be inductively coupled to a corresponding coil circuit in ultrasound probe 114.

Figure 11:
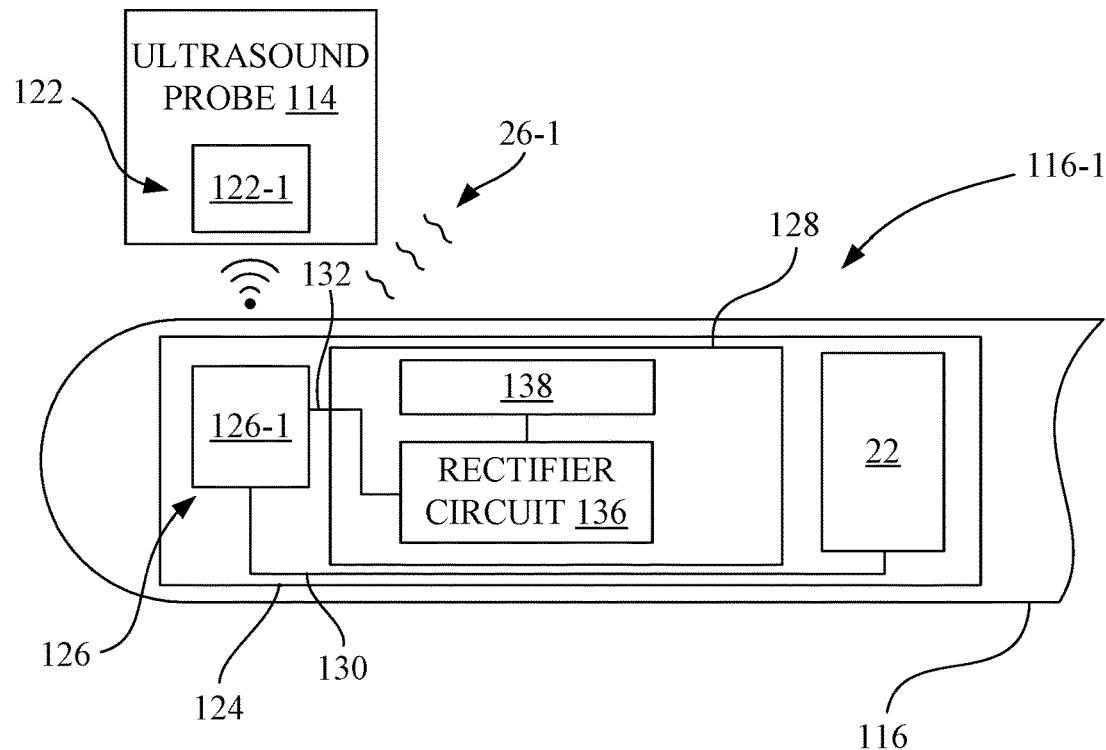
FIG. 11 is a graphical depiction of an enlargement of the distal portion of the interventional medical device having a tracking device that includes a tracking element, a wireless transmitter, and a power supply circuit having an excitation device to convert ultrasound sound waves into electrical power.

FIG. 11 shows an enlargement of the distal end portion 116-1 of interventional medical device 116 having tracking device 124, in accordance with another embodiment. In the embodiment of FIG. 11, the plurality of pickup coils 134 of the embodiment of FIG. 10 are replaced with an excitation device 138, e.g., an electromechanical device. Excitation device may be, for example, a piezoelectric generator circuit or a micro-cantilever generator circuit. Excitation device 138 is configured to receive ultrasound sound waves 26-1 of ultrasound imaging volume of ultrasound field-of-view volume 26 (see also FIG. 8) produced by ultrasound probe 114. Excitation device 138 is configured to convert the ultrasound sound waves 26-1 into electrical power, which in turn is sent to rectifier circuit 136, which in turn produces a DC power output that is supplied to near field transmitter circuit 126-1 of tracking device 124.

In addition to the configurations of power supply circuit 128 described above, it is contemplated that power supply circuit 128 may include a capacitor circuit having a capacitor that serves as an electrical energy storage device. For example, the capacitor may supplement the electrical power output of the plurality of pickup coils 134 of FIG. 10, or that of the excitation device 138 of FIG. 11, that is supplied to rectifier circuit 136 for providing electrical power to wireless transmitter 126, e.g., to near field transmitter circuit 126-1 of tracking device 124.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An imaging system,
comprising: an ultrasound probe comprising an ultrasound probe housing that includes an ultrasound transducer configured to generate an ultrasound field-of-view, a volume of the ultrasound field-of-view having a f first Z-axis defined on a first centroid of the ultrasound transducer, a tracking field generator to generate an electromagnetic locator field having a volume that is greater than the volume of the ultrasound field-of-view, and a wireless receiver, the tracking field generator configured to generate an electromagnetic locator field volume, wherein the tracking field generator comprises a plurality of electromagnetic coils including a first coil having a first axis parallel to an X-axis that is perpendicular to the first Z-axis, a second coil having a second axis parallel to a Y-axis that is perpendicular to the X-axis and the first Z-axis, and a third coil having a third axis that is parallel to the first Z-axis, such as that each of the first axis, the second axis, and the third axis correspond to a Cartesian coordinate system, the plurality of electromagnetic coils are positioned within a common plane that is parallel to a plane of the ultrasound transducer, wherein the plurality of electromagnetic coils surrounds the ultrasound transducer, each of the plurality of electromagnetic coils contained within the ultrasound probe housing, a second centroid of the plurality of electromagnetic coils collectively define a second Z-axis of the electromagnetic locator field volume, the ultrasound transducer and the plurality of electromagnetic coils are arranged within the ultrasound probe housing to facilitate an entirety of the ultrasound field-of-view located within the electromagnetic locator field and to coincide the first Z-axis of the volume of the ultrasound field-of-view with the second z-axis of the electromagnetic locator field volume during calibration of the ultrasound probe;
an interventional medical device having a distal end portion;
a tracking device mechanically coupled to the distal end portion of the interventional medical device, the tracking device including:
    a plurality of tracking coils to interact with the electromagnetic locator field to determine a location within the electromagnetic locator field volume and to generate tracking data,
    a wireless transmitter configured to transmit the tracking data from the tracking device of the interventional medical device to the wireless receiver of the ultrasound probe, and
    a power supply circuit configured to supply electrical power to the wireless transmitter of the tracking device.

2. The imaging system of claim 1, wherein the power supply includes pickup coils that are coupled to the interventional medical device at the distal end portion of the interventional medical device.

3. The imaging system of claim 1, wherein the wireless receiver is a near field receiver circuit and the wireless transmitter is a near field transmitter circuit, wherein the near field receiver circuit and the near field transmitter circuit utilize a near field communication protocol.

4. The imaging system of claim 1, wherein the wireless receiver includes a Bluetooth receiver circuit and the wireless transmitter includes a Bluetooth transmitter circuit, wherein the Bluetooth receiver circuit and the Bluetooth transmitter circuit utilize a Bluetooth communication protocol.

5. The imaging system of claim 1, wherein each of the wireless receiver and the wireless transmitter includes at least one of an inductive coupling circuit, an RF circuit, and an RFID circuit.

6. The imaging system of claim 1, wherein the power supply circuit of the tracking device includes a plurality of pickup coils at the distal end portion of the interventional medical device, the plurality of pickup coils configured to receive the electromagnetic locator field and convert a portion of the electromagnetic locator field into electrical power for use in satisfying the electrical power requirements of the wireless transmitter of the tracking device.

7. The imaging system of claim 1, wherein the power supply circuit of the tracking device includes an excitation device at the distal end portion of the interventional medical device, the excitation device configured to receive ultrasound sound waves in an ultrasound imaging volume from the ultrasound probe and convert the ultrasound sound waves into electrical power for use in satisfying the electrical power requirements of the wireless transmitter of the tracking device.

8. The imaging system of claim 7, wherein the excitation device is one of a piezoelectric generator circuit and a micro-cantilever generator circuit.

9. The imaging system of claim 1, wherein the power supply circuit of the tracking device includes an inductive coupling circuit.

10. The imaging system of claim 1, wherein the power supply circuit of the tracking device includes a capacitor circuit having a capacitor that serves as an electrical energy storage device.

11. An interventional medical device and imaging system, comprising:
    an ultrasound probe comprising an ultrasound probe housing that includes an ultrasound transducer configured to generate an ultrasound field-of-view, a volume of the ultrasound field-of-view having a f first Z-axis defined on a first centroid of the ultrasound transducer, a tracking field generator to generate an electromagnetic locator field having a volume that is greater than the volume of the ultrasound field-of-view, and a wireless receiver, the tracking field generator configured to generate an electromagnetic locator field volume, wherein the tracking field generator comprises a plurality of electromagnetic coils including a first coil having a first axis parallel to an X-axis that is perpendicular to the first Z-axis, a second coil having a second axis parallel to a Y-axis that is perpendicular to the X-axis and the first Z-axis, and a third coil having a third axis that is parallel to the first Z-axis, such as that each of the first axis, the second axis, and the third axis correspond to a Cartesian coordinate system, the plurality of electromagnetic coils are positioned within a common plane that is parallel to a plane of the ultrasound transducer, wherein the plurality of electromagnetic coils surrounds the ultrasound transducer, each of the plurality of electromagnetic coils contained within the ultrasound probe housing, a second centroid of the plurality of electromagnetic coils collectively define a second Z-axis of the electromagnetic locator field volume, the ultrasound transducer and the plurality of electromagnetic coils are arranged within the ultrasound probe housing to facilitate an entirety of the ultrasound field-of-view located within the electromagnetic locator field and to coincide the first z-axis of the volume of the ultrasound field-of-view with the second z-axis of the electromagnetic locator field volume during calibration of the ultrasound probe;
    an interventional medical device comprising an elongate body having a distal end portion and a tracking device mechanically coupled to the distal end portion of the interventional medical device, the tracking device including:
        a plurality of tracking coils contained within the distal end portion of the elongate body configured to determine a location of the tracking device within the electromagnetic locator field volume and to generate tracking data,
        a wireless transmitter configured to transmit the tracking data from the tracking device to the ultrasound probe, and
        a power supply circuit configured to wirelessly receive energy from the ultrasound probe, the power supply circuit configured to convert the energy into direct current voltage and current to supply electrical power to operate the wireless transmitter of the tracking device, the power supply circuit comprising a micro-cantilever generator circuit adjacent to the plurality of tracking coils and contained within the distal end portion of the elongate body, the micro-cantilever generator circuit configured to receive ultrasound sound waves in an ultrasound imaging volume from the ultrasound probe and convert the ultrasound sound waves into electrical power for use in satisfying the electrical power requirements of the wireless transmitter of the tracking device.

12. The interventional medical device and imaging system of claim 11, wherein the wireless receiver is a near field receiver circuit and the wireless transmitter is a near field transmitter circuit, wherein the near field receiver circuit and the near field transmitter circuit utilize a near field communication protocol.

13. The interventional medical device and imaging system of claim 11, wherein the wireless receiver includes a Bluetooth receiver circuit and the wireless transmitter includes a Bluetooth transmitter circuit, wherein the Bluetooth receiver circuit and the Bluetooth transmitter circuit utilize a Bluetooth communication protocol.

14. The interventional medical device and imaging system of claim 11, wherein each of the wireless receiver and the wireless transmitter includes at least one of an inductive coupling circuit, an RF circuit, and an RFID circuit.

15. The interventional medical device and imaging system of claim 11, wherein the power supply circuit of the tracking device includes a capacitor circuit having a capacitor that serves as an electrical energy storage device.

16. The imaging system of claim 1, further comprising:
    an ultrasound console coupled to the ultrasound probe, the ultrasound console comprising a graphical user interface.

17. The imaging system of claim 16, wherein the ultrasound console generates visual, tactile, or aural feedback to guide the ultrasound probe such that the distal end portion of the interventional medical device is included within the ultrasound field-of-view.

18. The imaging system of claim 17, wherein the ultrasound console generates visual feedback on the graphical user interface to guide the ultrasound probe.

\* \* \* \* \*